US00PP33073P3

(12) United States Plant Patent
Hand et al.

(10) Patent No.: US PP33,073 P3
(45) Date of Patent: May 18, 2021

(54) ***CANNABIS* PLANT NAMED 'MR2018002'**

(50) Latin Name: *Cannabis sativa*
Varietal Denomination: MR2018002

(71) Applicant: Aurora Cannabis Enterprises Inc., Edmonton (CA)

(72) Inventors: Andrew Hand, Bradford (CA); Alan Graziano, Toronto (CA)

(73) Assignee: Aurora Cannabis Enterprises Inc., Edmonton (CA)

( * ) Notice: Subject to any disclaimer, the term of this patent is extended or adjusted under 35 U.S.C. 154(b) by 0 days.

(21) Appl. No.: 16/873,050

(22) Filed: Jan. 21, 2020

(65) Prior Publication Data

US 2020/0236830 P1 Jul. 23, 2020

(30) Foreign Application Priority Data

Jan. 18, 2019 (CA) ..... PBR 19-9708

(51) Int. Cl.

| | |
|---|---|
| ***A01H 5/02*** | (2018.01) |
| ***A01H 6/28*** | (2018.01) |
| *A61K 36/185* | (2006.01) |

(52) U.S. Cl.

USPC ..... Plt./258

CPC ..... *A01H 6/28* (2018.05); *A61K 36/185* (2013.01)

(58) Field of Classification Search

USPC ..... Plt./258, 263.1

CPC ... A01H 5/02; A01H 5/00; A01H 5/12; A01H 6/28

See application file for complete search history.

*Primary Examiner* — Kent L Bell

(74) *Attorney, Agent, or Firm* — Christensen O'Connor Johnson Kindness PLLC

(57) ABSTRACT

A new cultivar of *Cannabis* plant named 'MR2018002' that is characterized by about 6% THC and 13% CBD by dry weight and resistance to microbial growth.

2 Drawing Sheets

Genus and species: *Cannabis sativa.*
Variety denomination: 'MR2018002'.

CROSS-REFERENCE TO RELATED APPLICATIONS

This application claims the benefit of priority under 35 U.S.C. 199(f) to Canadian Plant Breeders' Rights Application Number 19-9708, which was filed for the instant plant variety on Jan. 18, 2019.

BACKGROUND OF THE INVENTION

The present invention relates to a new and distinct *Cannabis* (*Cannabis sativa*) cultivar designated as 'MR2018002'.

'MR2018002' is a selection resulting from a controlled-cross between a male unnamed plant of *Cannabis sativa* variety of unknown background (unpatented) and a female unnamed plant of *Cannabis sativa* variety of unknown background (unpatented). The plants were grown in Markham, Ontario, Canada.

Seeds from the cross were sown and grown at an indoor *Cannabis* facility in Markham, Ontario, Canada. The plants were flowered under standard indoor environment conditions with High Pressure Sodium lamps. The plants were screened for a number of traits including tetrahydrocannabinol (THC) and cannabidiol (CBD) levels, yield, flowering time, disease resistance and flower morphology. An individual plant having about 6% THC and 13% CBD by dry weight and resistance to microbial growth was chosen to be 'MR2018002'.

In September 2016, 'MR2018002' was first asexually propagated by apical stem cuttings approximately 10 cm long and having multiple auxiliary meristems, in Markham, Ontario, Canada. 'MR2018002' is stable and reproduces true to type in successive generations of asexual reproduction. This cultivar has increased resistance to microbial growth for enhanced cultivation and production of flower yield and extracts thereof.

BRIEF SUMMARY OF THE INVENTION

This invention relates to a new and distinctive *Cannabis* cultivar designated as 'MR2018002'.

'MR2018002' exhibits about 6% THC and 13% CBD by dry weight. 'MR2018002' also exhibits microbial resistance.

BRIEF DESCRIPTION OF THE DRAWINGS

The accompanying color photographs depict characteristics of 'MR2018002.' The colors shown are as true as can be reasonably obtained by conventional photographic procedures. The photographs are of plants aged 53 days post-floral transition and grown in flower rooms under standard cultivation methods in Bradford, Ontario Canada.

DETAILED BOTANICAL DESCRIPTION

Figure 1:
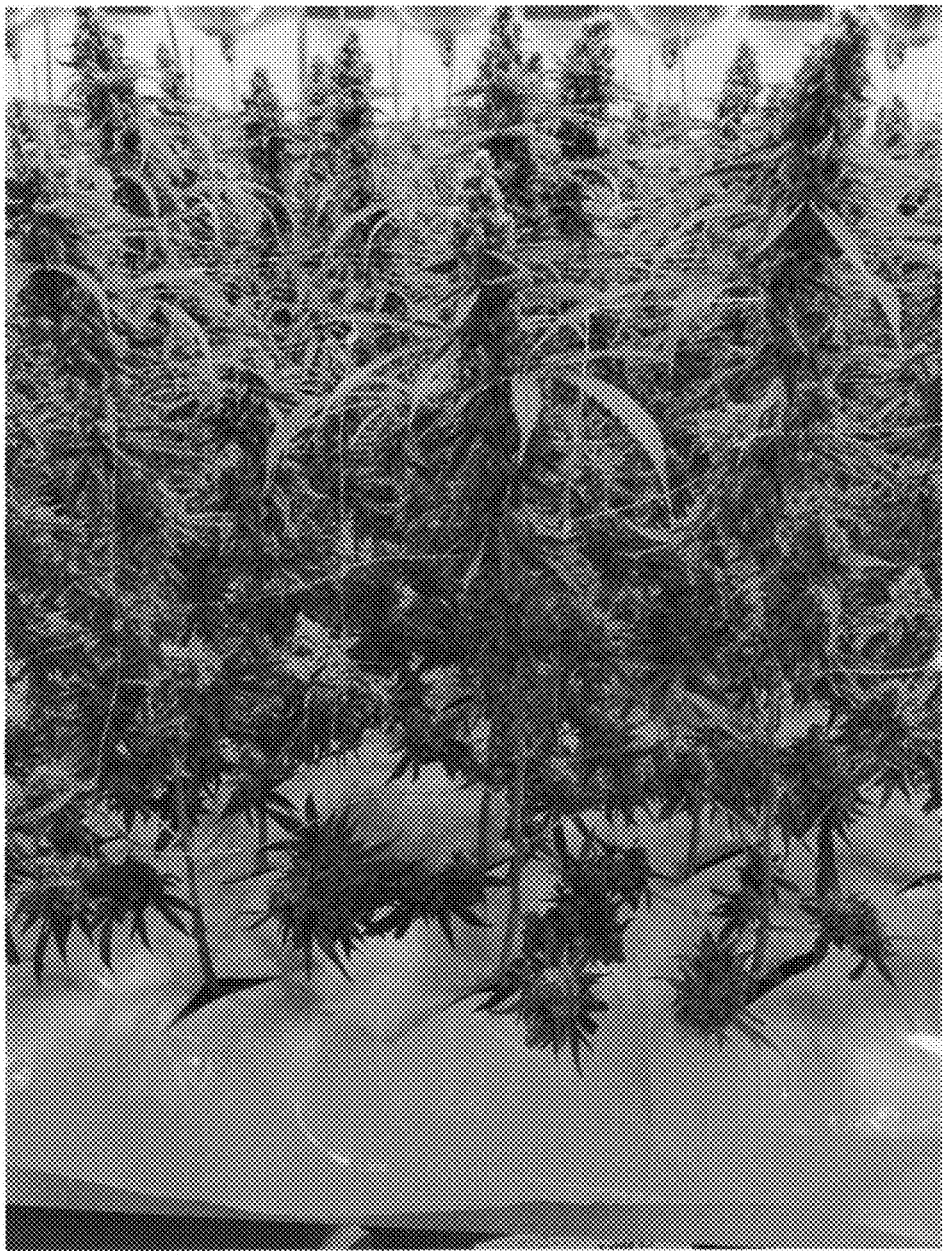
FIG. 1 shows multiple, whole plant clones of 'MR2018002'.
Figure 2:
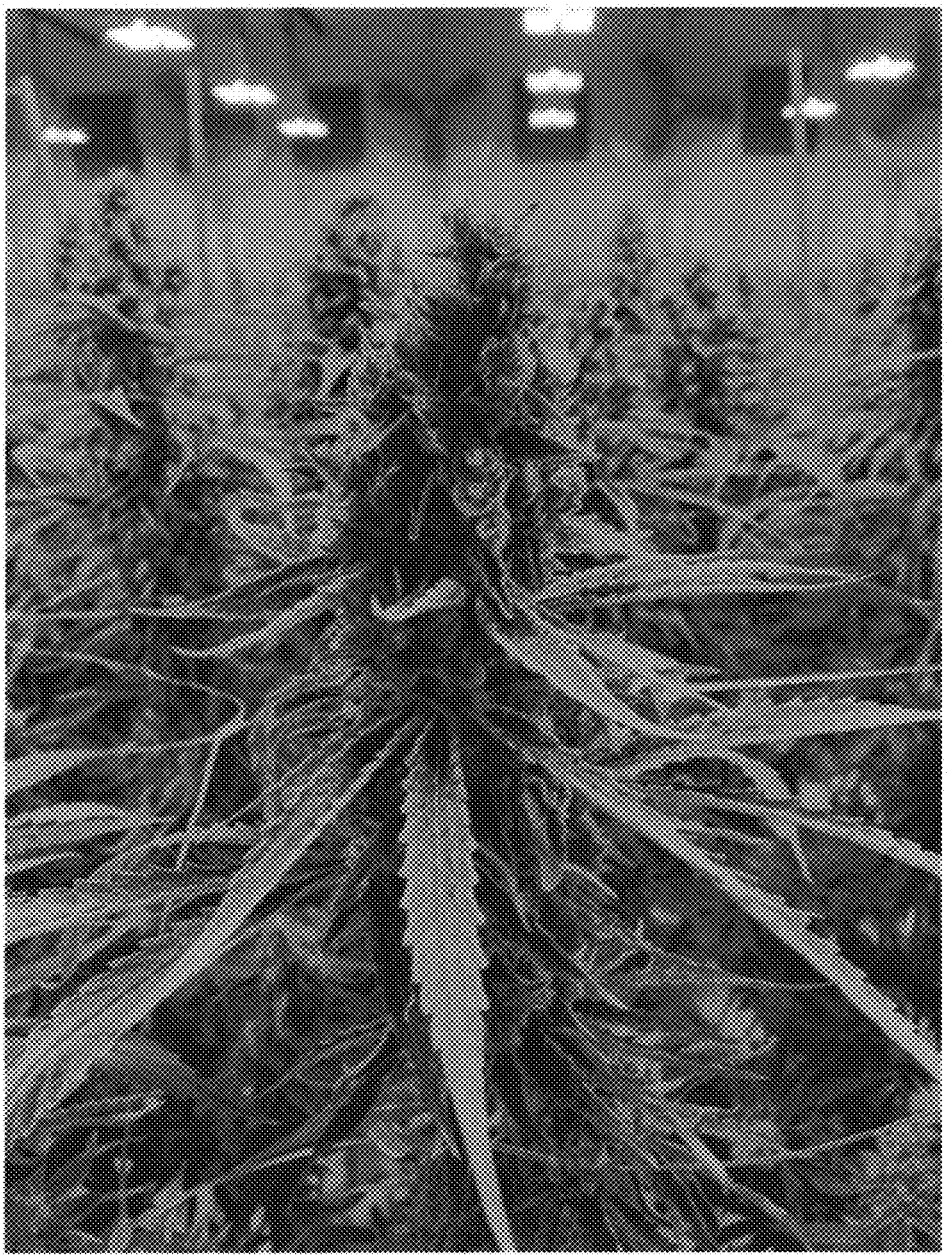
FIG. 2 shows a close-up view of an inflorescence and foliage of 'MR2018002'.

The following is a detailed description of the new cultivar 'MR2018002'.

'MR2018002' has not been tested under all possible environmental conditions. Phenotypic differences may be observed with variations in environment without any variance in genotype.

The traits of 'MR2018002' have been repeatedly observed and represent the distinguishing characteristics of 'MR2018002'.

The data that follows was collected in Markham, Ontario, Canada.

Plants were flowered under standard indoor environmental conditions with High Pressure Sodium lamps. Clones were cut from healthy mothers and allowed to root for 14 to 18 days prior to being introduced to the flower room. The room was maintained at 18 hour days/6 hour nights for a week to allow the cuttings to establish adequate vegetative tissue. The floral transition was initiated by switching to 12 hour days and 12 hour nights. Flowering lasted 8-9 weeks before harvest, at which point samples were taken for chemical analysis, and yield was quantified. Morphological measurements were taken from plants aged 7 weeks post-floral transition.

Standard in-house developed nutrients were used throughout growth, and the plants were defoliated and pruned as necessary throughout the cycle.

In the following description, the color determination is in accordance with the 2017 Munsell Plant Tissue Color Book, except where general color terms of ordinary dictionary significance are used.

Classification:

*Denomination*.—'MR2018002'.
*Family*.—Cannabacaeae.
*Genus*.—*Cannabis*.
*Species*.—*Cannabis sativa*.
*Common name*.—Marijuana.

Parentage: Male *Cannabis sativa* variety of unknown background and a female *Cannabis sativa* variety of unknown background.

Propagation: 'MR2018002' is asexually (clonally) propagated from vegetative cuttings. Roots are fine and well-branched. It takes approximately 14-18 days to produce a rooted young plant. Roots are fine and well-branched.

Plant:

*Height*.—65cm -75 cm.
*Width*.—Approx. 40 cm.

Stems:

*Length/height*.—50 cm-60 cm.
*Width/diameter*.—7 mm-9 mm.
*Color*.—2.5 GY 6/6, 5 RP 3/6.
*Shape*.—Tubular.
*Texture*.—Fibrous and Pubescent.
*Lateral branch length*.—25 cm-35 cm.

Foliage:

*Type/form*.—Palmately Compound.
*Arrangement*.—Alternate.
*Attachment*.—Petiolate.
*Leaf width*.—9 cm-14 cm.
*Leaf length*.—6 cm-15 cm.
*Number of leaflets per leaf*.—5-7.
*Leaflet shape*.—Lanceolate.
*Leaflet length*.—4 cm-14 cm.
*Leaflet width*.—1 cm-3 cm.
*Leaflet margin*.—Serrate.
*Leaflet apex*.—Acuminate.
*Leaflet base*.—Attenuate.
*Leaflet color, upper surface*.—7.5 GY 3/4, 7.5 GY 4/6.
*Leaflet color, lower surface*.—5 GY 5/4.
*Venation pattern and description, upper and lower leaflet surfaces*.—Pinnate.
*Texture* (*both surfaces*).—Pubescent, primarily on the abaxial side and along leaf vasculature.
*Stipules*.—Present, 2 per node on either side of a petiole, attenuated.
*Fragrance*.—Earthy, aromatic, herbal aroma.

Petiole:

*Length*.—1 cm-4.5 cm.
*Diameter*.—0.2 mm-0.29 mm.
*Texture*.—Fine, short non-glandular trichomes.
*Color*.—5 GY 6/6, 5 RP 3/6.

Inflorescence: The plant is a genetically female dioicous plant and, therefore, produces predominantly female flowers. There are no male-only plants. There is a very low incidence of hermaphroditism.

*Blooming habit*.—Short day photoperiod sensitive.
*Blooming period*.—51 days (average). Male flowering: male flowers are very rare; if present, typically develop between week 2 and 4 of general flowering.
*Attachment*.—Subsessile.
*Bracts*.—Covered with trichomes and resin glands with 2 to 3 stigmas.
*Bract color*.—5GY 7/8 (Munsell).
*Trichomes*.—Capitate-sessile, capitate-stalked, bulbous, and non-glandular (cystolith hairs); trichomes are present on almost all aerial organs but are present at highest concentration on female flowers (calyxes, bracts, etc.) as well as subtending intra-flower leaves.
*Bract trichome and resin gland color*.—Trichomes are clear, and will turn amber (approximately 10R 4/10 (Munsell)) during senescence.
*Inflorescence color*.—5 GY 5/8, 5 GY 5/10.
*Number of inflorescences per plant*.—18-35.
*Diameter*.—3 cm-6 cm.
*Length*.—4 cm-8 cm.
*Inflorescence anthocyanin*.—Absent for both female and male (very rare) flowers.
*Average flower width*.—3.7 cm.
*Inflorescence fragrance*.—Earthy, aromatic, herbal aroma.

Reproductive organs:

*Pistils*.—1.
*Quantity* (*of stigmas*) *per flower*.—2-4.
*Stigma length*.—0.4 cm-0.8 cm.
*Stigma width*.—0.7 mm-0.9 mm.
*Stigma color*.—2.5 GY 8/2, 7.5 YR 5/6.

THC and CBD content (quantified with a waters LC-MS/MS, running an acetonitrile:methanol:2-propanol gradient mobile phase through a raptor ACR-18, 2.7 um, 2.1×150 mm column):

*Average % THC by dry weight*.—6%.
*Average % CBD by dry weight*.—13%.

Yield:

*Average flower yield*.—642 g/m$^2$ (grams dried, trimmed flower per m$^2$ of growing space).
*Average trim yield*.—238 g/m$^2$ (grams trichome rich leaf material per m$^2$ that is removed during harvest/trimming).

Disease and insect/pest resistance: 'MR2018002' exhibits resistance to aerobic bacteria, yeast, mold and coliform bacteria as shown in Table 1.

TABLE 1

| 'MR2018002' resistance to aerobic bacteria, yeast, mold and coliform bacteria. | |
|---|---|
| Average Aerobic Bacteria Count (per plant, in colony forming units (CFUs)) | 4407.5 |
| Average Yeast and Mold Count (per plant, in CFUs) | 2057.5 |
| Average coliform bacteria count (per plant, in CFUs) | 10 |

COMPARISON WITH KNOWN VARIETY

A close variety of *Cannabis* known to the inventors is the commercial variety 'Girl Scout Cookies'. 'MR2018002' can be distinguished from 'Girl Scout Cookies' by its increased resistance to microbial growth, as shown in Table 2:

TABLE 2

Comparison between 'MR2018002' and 'Girl Scout Cookies': Microbial resistance

| Variety | # of Cycles Grown | Average Aerobic Bacteria Count* | Average Yeast and Mold Count** | Coliform Bacteria Count* |
|---|---|---|---|---|
| 'MR2018002' | 9 | 4407.5 | 2057.5 | 10 |
| Girl Scout 'Cookies' | 15 | 59270 | 52450 | 760 |

**Aerobic Bacteria Count, Yeast and Mold Count and Coliform Bacteria Count were determined per plant, in colony forming units (CFUs).

Variety 'MR2018002' can also be distinguished from the variety 'Girl Scout Cookies' with respect to the morphological traits shown in Table 3.

TABLE 3

Comparison between 'MR2018002' and 'Girl Scout Cookies': Morphological traits

| Characteristic | 'MR2018002' | 'Girl Scout Cookies' |
|---|---|---|
| Overage Average Height | 67.9 cm | 69.6 cm |
| Average Height | 68.7 cm | 74 cm |
| Average # of Nodes | 34.4 | 22.3 |
| Average Internodal Length | 4.6 cm | 6.6 cm |
| Average Flower Width | 3.7 cm | 5.3 cm |

In addition, the flowers produced by variety 'MR2018002' are denser and stickier than the flowers produced by 'Girl Scout Cookies'.

The invention claimed is:

1. A new and distinct cultivar of *Cannabis* plant named 'MR2018002' as described and illustrated herein.

* * * * *